(12) United States Patent
Nowakowski et al.

(10) Patent No.: US 6,482,223 B1
(45) Date of Patent: Nov. 19, 2002

(54) CLOTTING CASCADE INITIATING APPARATUS AND METHODS OF USE

(75) Inventors: Karol L. Nowakowski, Circle Pines, MN (US); James E. Olson, Eagan, MN (US); Edward T. Joseph, Inver Grove Heights, MN (US); Daniel G. Ericson, Rochester, MN (US)

(73) Assignee: Closys Corporation, Edina, MN (US)

( * ) Notice: Subject to any disclaimer, the term of this patent is extended or adjusted under 35 U.S.C. 154(b) by 65 days.

(21) Appl. No.: 09/585,488

(22) Filed: Jun. 1, 2000

Related U.S. Application Data

(63) Continuation-in-part of application No. 09/212,080, filed on Dec. 15, 1998, now Pat. No. 6,159,232.
(60) Provisional application No. 60/069,834, filed on Dec. 16, 1997, and provisional application No. 60/136,837, filed on Jun. 1, 1999.

(51) Int. Cl.[7] ............................................... A61B 17/04
(52) U.S. Cl. ..................... 606/213; 424/530; 210/782; 210/651; 422/44
(58) Field of Search ......................... 606/213; 424/529, 424/530; 210/782, 500.38, 651; 422/44

(56) References Cited

U.S. PATENT DOCUMENTS

| | | |
|---|---|---|
| 3,223,083 A | 12/1965 | Cobey |
| 4,277,463 A | 7/1981 | Tomic |
| 4,347,243 A | 8/1982 | Schneider |
| 4,359,049 A | 11/1982 | Redl et al. |
| 4,373,023 A * | 2/1983 | Langer et al. ................. 435/2 |

(List continued on next page.)

FOREIGN PATENT DOCUMENTS

| | | |
|---|---|---|
| EP | 0 466178 B1 | 6/1997 |
| JP | 406181979 | 7/1994 |

OTHER PUBLICATIONS

Effect of Delay and Storage on Whole–Blood Clotting Analysis as Determined by Thrombelastography, J. Clinical Monitoring, 1993, Vo. 9, pp. 5–8.

*Primary Examiner*—Gary Jackson
(74) *Attorney, Agent, or Firm*—Moore & Hansen

(57) ABSTRACT

Wound closure methods and apparatus are provided which utilize blood fluid by activating the clotting cascade of blood fluid outside the body within a substantially enclosed sterile container then introducing the blood fluid to the wound site to complete clotting. Methods and apparatus for providing ways of inhibiting anti-coagulating agents and slowing fibrin clot degradation are also disclosed. Kits for practicing the invention singularly or in combination with and/or associated with preferred procedures are also disclosed. The present invention provides improved methods of creating hemostasis or control of bleeding at the site of wounds, particularly wounds created in arteries during procedures employing percutaneous access. The invention preferably includes the steps of acquiring an aliquot of a patient's blood, i.e., autologous blood, removing a negatively charged anti-coagulating agent, preferably heparin, from the blood, and preferably initiating the blood's natural clotting cascades and transporting the thus treated blood to the site of the wound where the clotting cascade will be completed producing a clot at the wound site that will create a condition of hemostasis. The invention further provides a clotting cascade initiation apparatus including a substantially enclosed sterile containment chamber within which an aliquot of blood fluid, either autologous or from donor sources, can be received and retained. In preferred embodiments, the sterile containment chamber further includes a heparin binding agent which will bind heparin and remove it from the blood fluid. In further embodiments the containment chamber will also include a procoagulating agent, wherein a clotting cascade can be initiated when the blood fluid is accepted into the sterile containment chamber.

19 Claims, 4 Drawing Sheets

U.S. PATENT DOCUMENTS

| | | |
|---|---|---|
| 4,852,568 A | 8/1989 | Kensey |
| 5,000,854 A | 3/1991 | Yang |
| 5,151,192 A | 9/1992 | Matkovich et al. |
| 5,192,300 A | 3/1993 | Fowler |
| 5,292,332 A | 3/1994 | Lee |
| 5,310,407 A | 5/1994 | Casale |
| 5,318,524 A | 6/1994 | Morse et al. |
| 5,383,896 A | 1/1995 | Gershony et al. |
| 5,413,571 A | 5/1995 | Katsaros et al. |
| 5,437,292 A | 8/1995 | Kipshidze et al. |
| 5,443,481 A | 8/1995 | Lee |
| 5,447,502 A | 9/1995 | Haaga |
| 5,275,616 A | 1/1996 | Fowler |
| 5,510,102 A | 4/1996 | Cochrum |
| 5,529,577 A | 6/1996 | Hammerslag |
| 5,532,311 A | 7/1996 | Sirvio et al. ............... 525/54.2 |
| 5,571,181 A | 11/1996 | Li |
| 5,585,007 A | 12/1996 | Antanavich et al. |
| 5,591,205 A | 1/1997 | Fowler |
| 5,601,602 A | 2/1997 | Fowler |
| 5,624,669 A | 4/1997 | Leung et al. |
| 5,674,394 A | 10/1997 | Whitmore |
| 5,676,689 A | 10/1997 | Kensey et al. |
| 5,716,375 A | 2/1998 | Fowler |
| 5,741,223 A | 4/1998 | Janzen et al. |
| 5,788,662 A | 8/1998 | Antanavich et al. |
| 5,795,571 A | 8/1998 | Cederholm-Williams et al. |
| 5,814,066 A | 9/1998 | Spotnitz |
| 5,830,130 A | 11/1998 | Janzen et al. |
| 5,843,124 A | 12/1998 | Hammerslag |
| 5,916,236 A | 6/1999 | Van de Moer et al. |
| 5,957,952 A | 9/1999 | Gershony et al. |
| 6,007,563 A | 12/1999 | Nash et al. |
| 6,033,427 A | 3/2000 | Lee |
| 6,146,771 A | 11/2000 | Wirt et al. .................. 428/515 |
| 6,197,289 B1 * | 3/2001 | Wirth et al. ............. 424/78.08 |

* cited by examiner

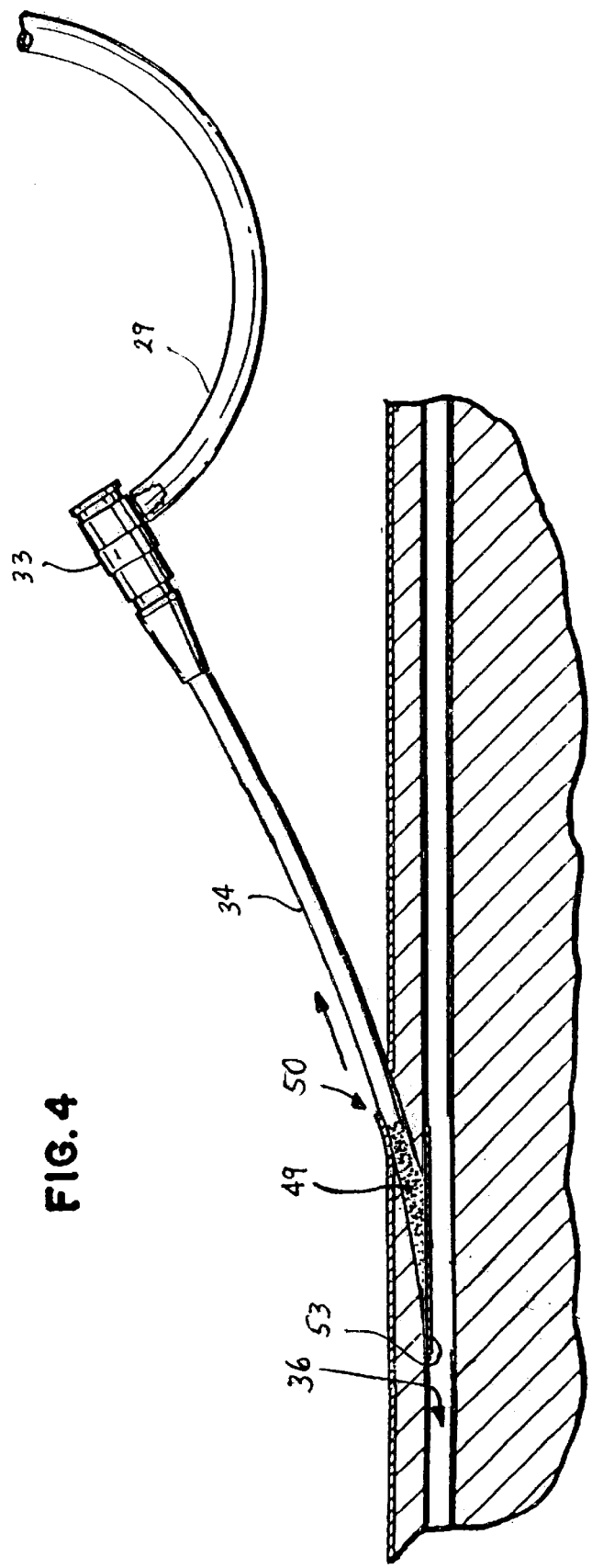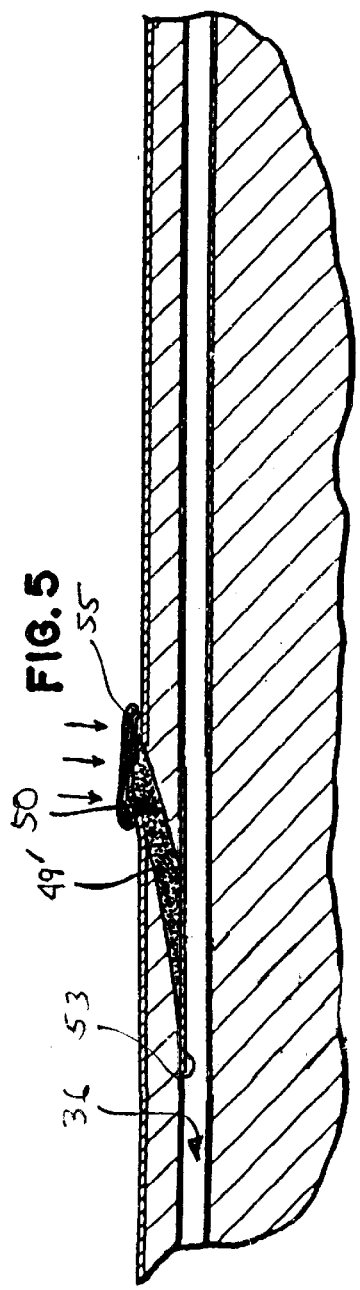

CLOTTING CASCADE INITIATING APPARATUS AND METHODS OF USE

CROSS-REFERENCE TO OTHER APPLICATIONS

The present application is a Continuation-In-Part Application of pending U.S. patent application Ser. No. 09/212,080 entitled Clotting Cascade Initiating Apparatus And Methods Of Use And Methods Of Closing Wounds, filed Dec. 15, 1998, now U.S. Pat. No. 6,159,232, which claims priority to U.S. Provisional Patent Application Serial No. 60/069,834 entitled Vascular Wound Closure, filed Dec. 16, 1997. A further claim of priority is also made to U.S. Provisional Patent Application Serial No. 60/136,837 entitled Heparin Reversal Blood Drawing Apparatus filed Jun. 1, 1999.

BACKGROUND OF THE INVENTION

The present invention relates to a novel apparatus and method for surgical wound closure applications. Numerous medical applications exist where sealing of biological tissue is desired. U.S. Pat. No. 5,510,102 to Conchrum identifies a variety of applications including traumas of the liver, spleen, pancreas, lung, bone, etc.; cardiovascular and vascular applications, such as microvascular anastomoses, vascular grafts, intraoperative bleeding and aortic repair; and the like.

The described invention provides a means to remove the heparin from anticoagulated whole blood. A sample of blood intended for either diagnostic analysis or therapeutic use is drawn into a blood collection apparatus. The blood is exposed to a material that has an immobilized substrate that removes a negatively charged anti-coagulating agent, preferably heparin, from the ample. Blood drawn into and across the immobilized biomaterial will be de-heparinized, and therefore will be capable of clot formation.

The most prominent application is sealing of a vascular wound resulting from percutaneous entry, as is frequently encountered in angiography, angioplasty and atherectomy procedures. Percutaneous vascular access is typically required in the context of minimally invasive surgical procedures. These techniques are often used to reduce trauma to the patient. Reduced trauma typically translates to improved patient comfort, minimized procedural complications, and lower costs. The vessel accessed is typically the femoral or radial artery. Access involves placement of an introducer's distal tip beneath the patient's skin and through the arterial wall. To the extent possible, percutaneous access preserves the integrity of the tissue covering the artery. As a result, when the introducer is to be removed, the arterial access site is not exposed and the arterial wound is preferably closed without cutting down though the overlaying tissue to expose the site.

To accomplish hemostasis at the wound, numerous methods of post-introducer arterial closure have been tried. The prior art devices used in these methods may be broadly classified into two groups, those that mechanically achieve hemostasis and those that rely on clotted blood or components of blood to form all or a part of the hemostatic agent. By example, sutures, whether placed through an open surgical exposure of the artery or by means of a device designed to place sutures percutaneously are associated with mechanical methods, as these methods rely on mechanically closing the opening in the artery. The second group, those using clotted blood, include the predominant method of treatment, manual compression of the wound site. In this method, after the effects of any anti-coagulating drugs have worn off, an attendant applies compression to the wound site until a clot of sufficient strength has formed to stop bleeding. Alternatively, the attendant may apply any of various mechanical devices that will hold compression, such as a sand bag or a pneumatic clamp, until hemostasis is achieved.

Recently, a variety of devices have entered the market that aid in achieving hemostasis, even in the event of a patient whose blood is still actively anti-coagulated. These devices typically rely on mechanical methods such as sutures or upon various biologic substances, such as collagen and thrombin, that are known to induce clotting of blood even when anti-coagulating agents are present. The differences between the devices is largely in the delivery platforms used to position the biologic materials. Disadvantages of the prior art devices and methods vary depending on the method employed. Generally speaking, mechanical devices that deploy sutures are complex, expensive and technically difficult to employ. In addition, mechanical closure of the opening in an arterial wall can lead to a permanent restriction at that site as the diameter of the artery is reduced when the opening is pulled together, much like a purse string. Open vascular access closure by means of suturing requires the skill of a specialist, a vascular surgeon, a specialist not required for the procedure itself and, therefore, an additional expense. Suturing by means of a specially designed percutaneous device offers the advantage of a very rapid cessation of bleeding through the arteriotomy, but can lead to significant issues if the device malfunctions and becomes entangled in place. In addition, secondary bleeding, that from the capillary bed of the adjacent soft tissue, can be left untreated. This secondary bleeding can continue for extended periods, causing weeping at the wound site and potentially leading to infections.

Current methods which rely in whole or in part on clotted blood also suffer from significant drawbacks. The compression method requires that the patients blood return to normal clotting status by means of the natural metabolization of anti-coagulating drugs. This process can take several hours, a period during which the patient must remain in the vicinity of the catheterization lab with the procedural sheath still in place. The compression period, once it begins, can last for extended periods, sometimes more than two hours. This process is uncomfortable for the patient, often painful, and it is tedious for the attendant or attendants as well. In addition, hemorrhaging can occur if the site is not held properly or if the compression period is terminated too early. Also, due to the time involved, both in terms of attendant time and cath lab time, this process tends to be quite expensive.

The devices which have been designed to be used in association with methods which improve on devices using clotted blood, generally work in a more rapid manner, but not without additional risks. The biologic materials employed, collagen and thrombin, are very potent clot inducing substances, so much so that if they are inadvertently deployed into the artery rather than outside, adjacent to the artery, a limb or life threatening clot may form inside of the artery. This condition can be difficult to treat and, in the best of circumstances, require dramatic, extensive intervention. In addition, the biologic materials used are derived from animal sources, typically bovine, and, therefore, bring along other inherent risks associated with such sources. Included among these risks are allergic reactions and the possibility of contracting bovine spongiform encepholapathy (BSE), otherwise known as mad cow's disease. The prior art devices are often technically difficult to use and their use can inhibit reaccess at the same site in situations where an additional procedure needs to be performed on the patient, such as in an emergency follow-up procedure. Transmission of infectious disease can also occur when the material used is manufactured from pooled human blood as reported in Opth. Surg., 3:640 (1992). Autologous preparations like fibrin glue, as described in U.S. Pat. No. 5,674,394 to Whitmore, are well known, but significant preparation, with the associated labor and material costs, is required and typically an additional thrombin material is still required at the wound site.

Despite the need for a device and a method which overcomes the limitations of the prior art, the prior art devices and methods have failed to adequately address the needs for a rapid and efficacious method of closing vascular and other wounds. Accordingly, it will be appreciated that there is a need for an efficient way of closing wounds. The present inventions provide advantages over the prior devices and the prior methods used to close wounds, and also offer other advantages over the prior art and solve other problems associated therewith.

SUMMARY OF THE INVENTION

The present invention provides improved methods of creating hemostasis or control of bleeding at the site of wounds, particularly wounds created in arteries during procedures employing percutaneous access. The invention preferably includes the steps of acquiring an aliquot of a patient's blood, i.e., autologous blood, removing a negatively charged anti-coagulating agent, preferably heparin, from the blood, and preferably initiating the blood's natural clotting cascades and transporting the thus treated blood to the site of the wound where the clotting cascade will be completed producing a clot at the wound site that will create a condition of hemostasis. The invention further provides a clotting cascade initiation apparatus including a substantially enclosed sterile containment chamber within which an aliquot of blood fluid, either autologous or from donor sources, can be received and retained. In preferred embodiments, the sterile containment chamber further includes a heparin binding agent which will bind heparin and remove it from the blood fluid. In further embodiments the containment chamber will also include a procoagulating agent, wherein a clotting cascade can be initiated when the blood fluid is accepted into the sterile containment chamber. Once the clotting cascade is initiated, the blood fluid is returned to the wound within the patient such that the clotting cascade can be completed and a clot can form within the wound. The invention further provides a method of using the clotting cascade initiation apparatus of the present invention to close a wound preferably including the step of drawing an aliquot of the patient's blood fluid. The invention further provides a method of using the clotting cascade initiation apparatus, preferably including providing a kit, preferably including providing a preferred sterile containment chamber and a vascular sheath for drawing an aliquot of blood fluid, preferably autologous blood fluid from the patient, and said blood fluid to a wound site within a patient once a substantial percentage of any heparin within the blood fluid drawn into the sterile containment chamber has been removed from the blood fluid within the sterile containment chamber, and once the clotting cascade has been initiated within such blood fluid. The invention further provides a method to initiate the natural intrinsic clotting cascade mechanism of human blood, wherein the intrinsic clotting cascade mechanism can be initiated when the blood is accepted into the sterile containment chamber, this blood with the intrinsic clotting cascade mechanism being useful when delivered to the wound site from the apparatus, where the natural extrinsic clotting mechanism is activated. This blood, with both the natural intrinsic and extrinsic clotting mechanisms being activated, then completes the clotting cascade process once delivered to the wound site, thus forming a clot of sufficient strength to stop blood flow from the wound site. Alternate embodiments of the invention provide methods to inactivate or remove the anti-clotting drug heparin by binding the heparin and removing it from the blood. The invention provides the methods to activate the natural intrinsic clotting cascade mechanism by means of activating blood factor XII by exposure to sufficient, specific biomaterial surface contact; and blood factor VIII by way of introducing sufficient mechanical shear. The invention further provides the method to activate and benefit from the natural extrinsic clotting cascade mechanism by means of blood factor VII activation from wound tissue contact. The described invention provides a means to remove the heparin from anticoagulated whole blood. The blood is exposed to a material that has an immobilized substrate that removes a negatively charged anti-coagulating agent, preferably heparin, from the sample. Blood drawn into and across the immobilized biomaterial will be de-heparinized, and therefore will be capable of clot formation.

It is believed that the present invention offers significant advantages over the prior art methods and devices. The use of naturally clotted blood as a hemostatic agent is the way nature intended wounds to be sealed and is the means proven most safe and reliable in standard hospital practices. By substantially removing the anti-coagulating agent heparin from blood, whether autologous or from donor sources, the blood is returned to a condition where natural clotting activities can occur and be manipulated. By controlled and measured initiation of the intrinsic clotting cascade mechanism, blood factors VIII and XII can be activated, thus producing a blood sample that will, in a predictable time frame, advance towards a completed clot. This process is further enhanced when the blood sample is returned or placed in the body in the soft tissue adjacent to the arteriotomy. Contact of such de-heparinized blood, while it is still in a fluid phase, with the exposed surfaces of the tissue will initiate the extrinsic clotting cascade mechanism as controlled by blood factor VII. This now fully treated blood, preferably with virtually all traces of heparin inactivated or removed, and both the intrinsic and extrinsic pathways activated, whereby preferably blood factors VII, VIII and XII have all been activated, will quickly transform from fluid phase blood to a solid phase blood clot of sufficient strength and quantity to create a condition of hemostasis. In the event that the activated blood is inadvertently deployed to one degree or another into the accessed blood vessel, rather than just adjacent to it, the blood deposited inside the vessel will not progress to form a clot, but merely mixes with the blood within the vessel and dissipates in the blood. The treated blood within the wound, however, will complete the clotting process and fibrin clot will form to close the wound and stop the flow of blood through the wound.

As used herein, the following terms have the following meanings: "Blood fluid" means whole blood or a fluid containing natural components of whole blood, whether derived from whole blood, whole blood extracts, or products of ex vivo cell cultures, the blood fluid containing sufficient blood components to enable a portion of the blood fluid to clot subsequent to the initiation of a clotting cascade; "Clotting cascade(s)" means a sequential series of chemical, proteolytic/enzymatic reactions naturally occurring which, if not inhibited or interrupted, result in clot formation;

"Clot" means a solidified mass of blood fluid having most of the available fibrin polymer cross-linked; "Biocompatible" means an agent is regarded by the regulating government body to be acceptable for use in the human body; "Procoagulant" means any process, activity, material or substance that serves to initiate, continue or accelerate a clotting cascade; "Anti-coagulating agent" means a component capable of preventing blood fluid clot formation. All patents, patent applications, and references cited herewith are hereby incorporated by reference.

These and various other advantages and features of novelty that characterize the present invention are pointed out with particularity in the claims annexed hereto and forms a part hereof However, for a better understanding of the present invention, its advantages and other objects obtained by its use, reference should be made to the drawings, which form a further part hereof and to the accompanying descriptive matter, in which there is illustrated and described preferred embodiments of the present invention.

BRIEF DESCRIPTION OF THE DRAWINGS

The invention will be further described in connection with the accompany drawings, in which:

FIG. 4 is a cross-sectional view of a blood vessel within a portion of the body tissue of a patient similar to that shown in FIGS. 1–3, in which the sheath is being removed from the body tissue as initiated blood, which has begun to clot as it is delivered through the sheath to the wound site, is forced out of the sheath into the wound site; and FIG. 5 is a cross-sectional view of a blood vessel within a portion of the body tissue of a patient similar to that shown in FIGS. 1–4, except that the sheath has been fully removed from the wound site and the initiated blood, delivered to the wound site as the sheath is removed, has clotted to block the flow of blood (not shown) from the blood vessel through the wound site.

DETAILED DESCRIPTION OF THE PREFERRED EMBODIMENTS

Figure 1:
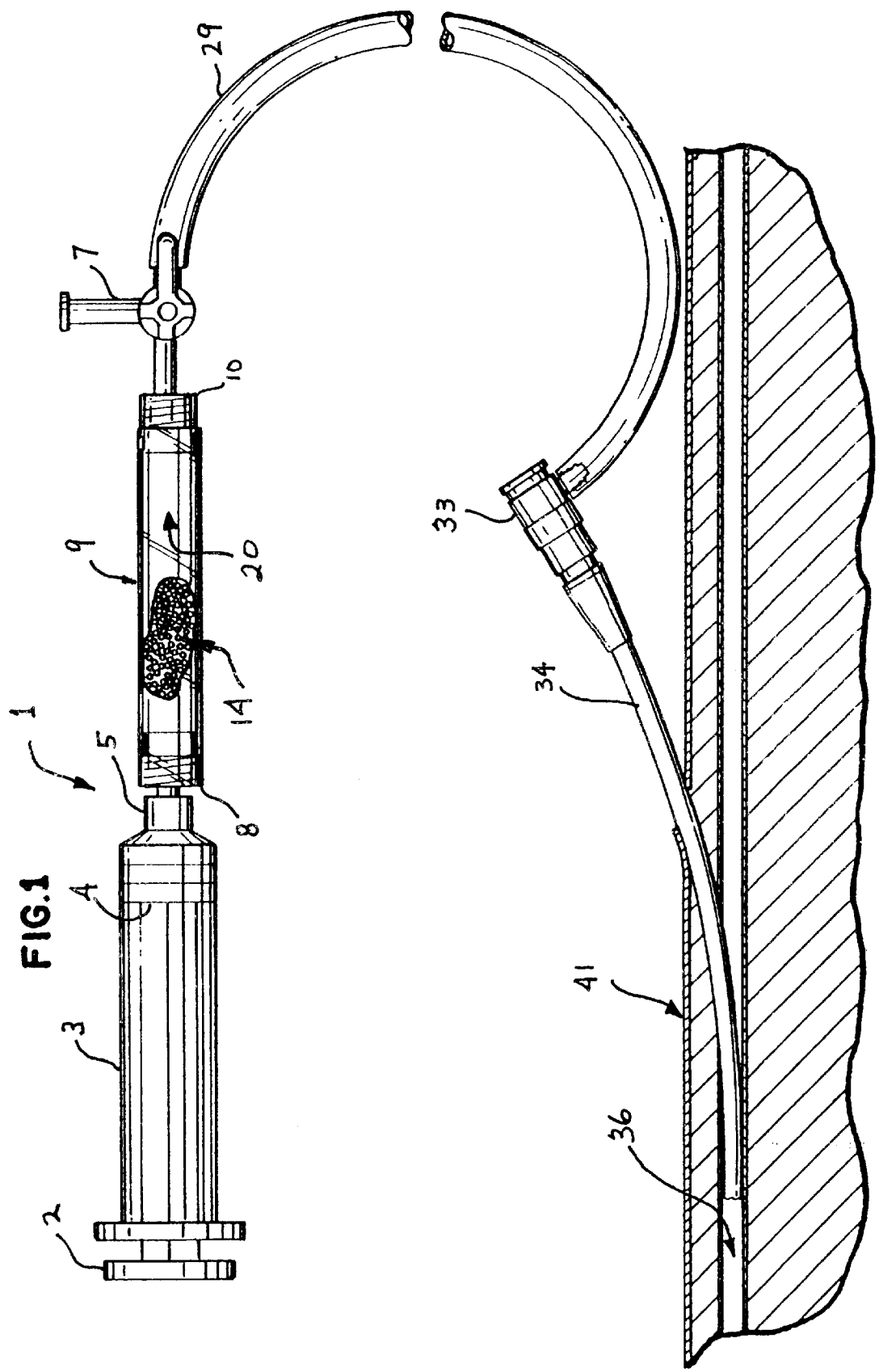
FIG. 1 is a clotting cascade initiation apparatus of the present invention interconnected with a hemostasis valve and a valve sheath by a side-arm in a manner in which the clotting cascade initiation apparatus would be interconnected in order to draw blood fluids from a blood vessel (shown in cross-section) within a portion of the body tissue of a patient.

Referring now to FIG. 1, a preferred embodiment of the present clotting cascade initiation device 1 is shown in fluid communication with a hemostasis sheath 34 having a hemostasis valve 33 interconnected with the clotting cascade initiation device 1 via a side-arm 29. The clotting cascade initiation device 1 shown in FIG. 1 includes a syringe 3 having a plunger 2 which slides tightly against the inner walls of the syringe 3, enabling one to draw fluids into the syringe when the plunger 2 is drawn back. The syringe is preferably interconnected with a cartridge 9 containing a sterile containment chamber 20 the cartridge 9 is interconnected with the side arm 29 by a stop cock 7 adding a luer fitting for engagement with the cartridge 9. When the stop cock 7 is in the open position as shown in FIG. 1, blood (not shown) may be withdrawn from the blood vessel 36 shown in cross-section within a portion of a patient's body 41 when the plunger 2 is partially withdrawn from the syringe 3 to create a vacuum in the syringe 3 which draws blood (not shown) from the blood vessel 36 through the hemostasis sheath 34, the side arm 29, the stop cock 7 and the sterile containment chamber 20 within the cartridge 9 before entering the syringe 3. As the blood passes through the sterile containment chamber 20 it passes over the surfaces of a porous matrix of glass beads 14 within the sterile containment chamber 20. The glass beads are preferably coated with a positively charged polymer which binds negatively charged molecular species such as heparin which is often found in blood of patients being treated in surgical procedures and the like. As the blood passes over the surfaces within the porous matrix, the positively charged polymeric coating will preferably bind heparin found in the blood and remove it from the blood. At the same time, the shear created by the passage of the blood fluid across the surfaces of the glass beads will initiate certain elements of the clotting cascade and begin the natural process of clotting the blood by so initiating the clotting cascade.

Figure 2:
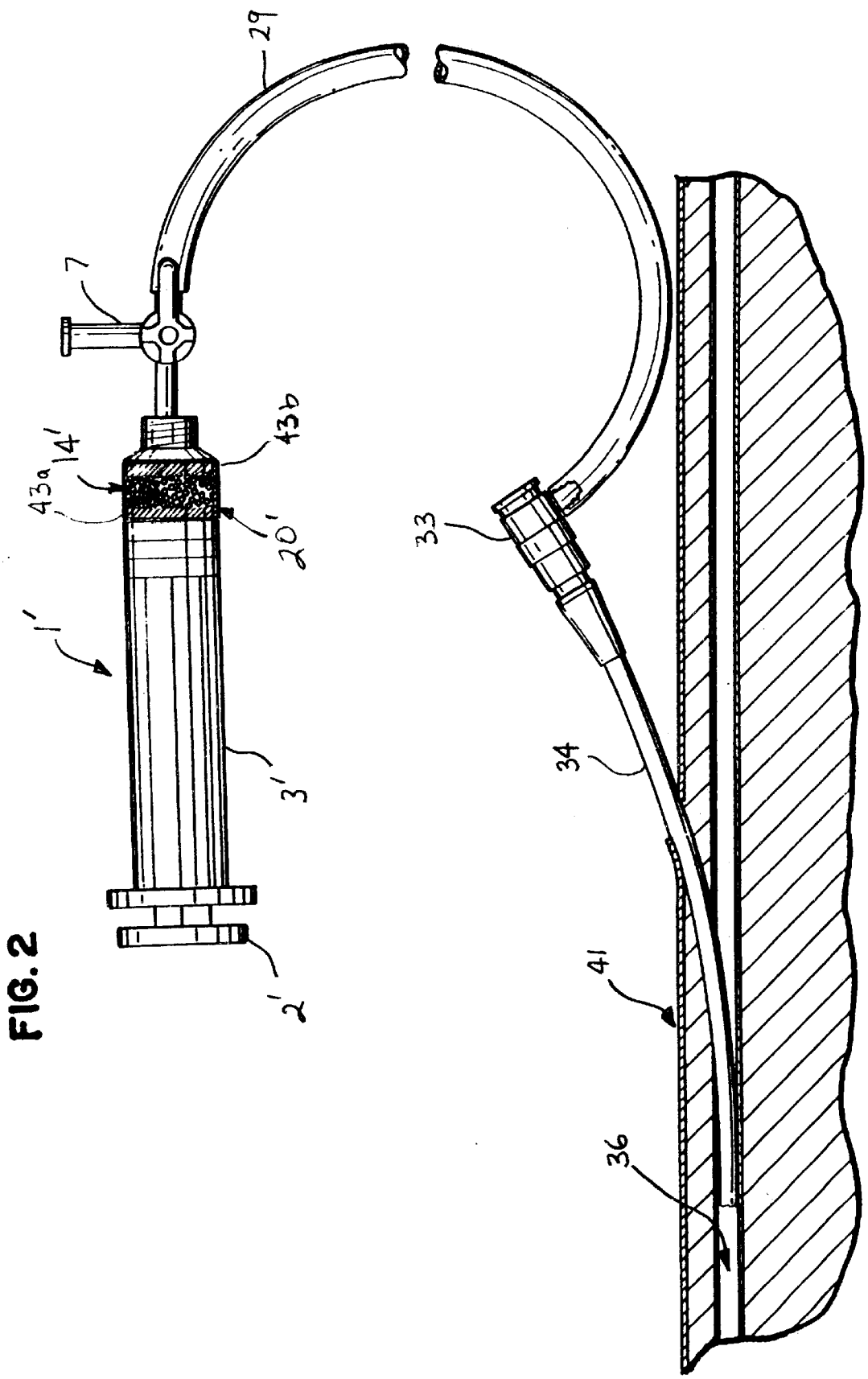
FIG. 2 is an alternate embodiment of the present clotting cascade shown in a manner similar to that shown in FIG. 1.

Referring now also to FIG. 2, an alternate clotting cascade initiation device 1' is shown in communication with a hemostasis sheath 34 interconnected with the clotting cascade initiation device 1' via the side arm 29 and the stop cock 7. In this embodiment, the glass beads 14' are located within a sterile containment chamber 20' within the syringe. A pair of porous filters 43a and 43b, respectively allow blood to pass through while retaining any solids larger than the filter pore size, including the glass beads 14' which are preferably coated with a positively charged coating polymer which will bind heparin and substantially remove the heparin from any blood passing through the porous matrix created by the glass beads 14'. Similarly, the clotting cascade in blood passing through the porous matrix created by the glass beads 14' will be initiated as the blood passes over the surfaces of the coated glass beads 14'. In further embodiments (not shown), uncoated glass beads (not shown) may be used to initiate the clotting cascade, however, if the blood contains a significant amount of heparin, the heparin will generally prevent the blood from clotting so long as it is present in the blood and is not either removed or inactivated.

Figure 3:
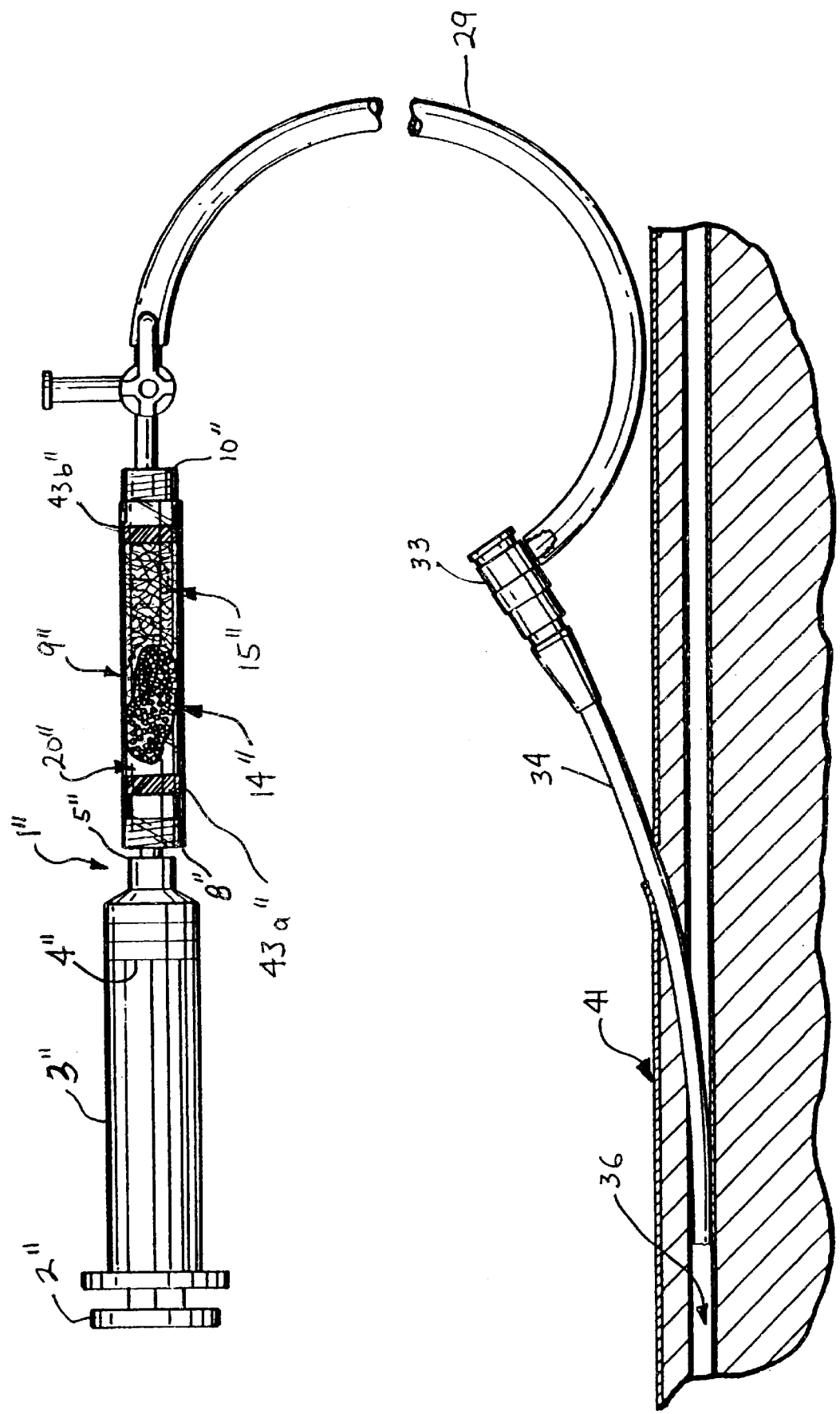
FIG. 3 is a further alternate embodiment of the present clotting cascade initiation apparatus shown in a manner similar to that shown in FIGS. 1 and 2.

Referring now also to FIG. 3, a further alternate embodiment of the present invention, shown in FIG. 3 includes a clotting cascade initiation device 1" in which a preferred cartridge 9" includes a porous matrix made up of coated glass beads 14" and a porous matrix of biomaterials 15" within the sterile containment chamber 20". The porous matrix of coated glass beads 14" and the porous matrix of biomaterials 15" are retained within the sterile containment chamber 20" by a pair of porous membranes 43a" and 43b" approximate respective ends of the cartridge 9". The porous membranes 43a" and 43b" preferably have sufficiently small pores to prevent the coated glass beads 14" or fibers within the porous biomaterials 15" from passing through the porous membranes 43a" and 43b".

It will be appreciated that other embodiments of the present invention not shown or discussed in detail in the present disclosure, nevertheless fall within the broad scope of the present invention so long as the clotting cascade initiation device contains an agent or agents within a sterile containment chamber which either binds a negatively charged anti-coagulating agent or drug such as heparin, hirudin or the like so as to substantially reduce the anti-coagulating agent concentration in blood passing through the sterile containment chamber or contains an agent which degrades, neutralizes, cleaves, digests, or by other means inactivates the anti-coagulating agents so as to effectively reduce the active anti-coagulating agent concentration within the blood passing through the sterile containment chamber and effectively reduce the activity of the agent in preventing the blood from clotting. As used herein, the term "negatively charged" refers to something that has a negative charge when located in an aqueous solution or and aqueous system such as blood or a blood fluid. Heparin and hirudin are negatively charged anti-coagulating agents. The negatively charged anti-coagulating agent generally encountered in human blood fluids is heparin. In preferred embodiments, the sterile containment chamber or a further sterile containment chamber removed from the first containment chamber containing the heparin binding or heparin neutralizing agent, will contain a biomaterial which enhances the initiation of the clotting cascade so that the blood will clot in a shorter period of time than it might in the absence of the biomaterial once the effective concentration of heparin in the blood is substantially reduce by the heparin binding or heparin neutralizing agent or agents. In the various embodiments of the present invention, there are a number of polymeric materials which can be attached to a number of substrates in order to immobilize these agents to enhance their ability to bind heparin and remove the heparin from blood passing through the alternate sterile containment chambers of the various embodiments of the present invention. Similarly, there are numerous biomaterials which will have comparable clotting cascade initiating events. Other procoagulating or procoagulant substances or mechanical stresses may be employed to accelerate the clotting cascade in blood treated within the alternate sterile containment chambers of the present invention. Discussions of a number of alternate embodiments of the present invention will follow. It will be appreciated that the present invention encompasses any combination of the elements of the various embodiments discussed below.

Referring now also to FIGS. 4 and 5, it will be appreciated that a preferred method of closing a wound in a patient in accord with the present invention comprises the steps of: treating a blood fluid with an agent which substantially reduces the anticoagulation effect in the blood fluid prior to treatment, the agent interacting with heparin in the blood fluid in a manner selected from the group consisting of binding to the anti-coagulating agent so as to remove the anti-coagulating agent from the blood fluid, degrading, immobilizing or neutralizing molecules so as to make them ineffective as an anti-coagulating agent and binding to the heparin so as to make the heparin molecules substantially ineffective as an anti-coagulating drug which can either inhibit or impede either the initiation or the continuance of the clotting cascade; and transporting the treated blood fluid to the wound in the patient such that the blood fluid comes into contact with the patient approximate the wound and the clotting cascade comes generally to a conclusion and a clot forms approximate the wound such that the clot is formed and the clot prevents fluid from passing through the wound. In preferred embodiments, the step of treating the blood fluid includes treating the blood fluid with a procoagulating agent to initiate a clotting cascade during a first time period such that at least a portion of the blood fluid will form a clot of blood during a second time period subsequent to the first time period, the blood fluid containing sufficient blood components to enable a portion of the blood fluid to clot during the second time period subsequent to the initiation of the clotting cascade during the first time period; the blood fluid being selected from the group whole blood, natural components of whole blood, whether derived from whole blood, blood extracts, or products of ex-vivo cell cultures, and procoagulating agents which assist in or enhance the clotting or coagulation of the blood fluids, the step of treating the blood fluid initiating the clotting cascade.

In preferred embodiments autologous blood is drawn from the patient and exposed to a porous matrix within which is contained such an agent which substantially reduces the anticoagulation effect of heparin present in the blood fluid prior to such treatment. In preferred embodiments this autologous blood is subsequently returned to the wounds site in the manner shown in FIG. 4 where the sheath is being removed from the blood vessel 36 and the wound proximate the arteriotomy as blood fluids so treated are returned to the wound site following treatment of the blood fluid with an agent which substantially reduces the anticoagulation effect of the heparin present in the blood fluid prior to such treatment and preferably provides a blood fluid in which the clotting cascade has been initiated such that the blood fluid will clot after being delivered to the wound site. In FIG. 4 a fibrin clot 49 is shown as it is beginning to knit together within the wound site 50. Once the sheath 34 is completely removed from the wound site 50, as shown in FIG. 5, a piece of sterile gauze 55, sterile cotton or the like is preferably placed upon the exterior of the tissue proximate the wound site 50 so that downward pressure (denoted by the three arrows proximate the wound site) may be applied to the wound site 50 for about 3 to 5 minutes to impede any potential flow of blood fluid through the wound site and enhance the ability of the fibrin clot 49 to continue to knit together as the clotting cascade continues to proceed to a conclusion where the clotting cascade is completed and the fibrin clot 49 is fully formed as shown in FIG. 5.

The present invention provides novel methods and apparatii for use in achieving hemostasis and wound closure in wounds in tissues. The invention preferably neutralizes or substantially eliminates the effect of anti-coagulating agents, such as heparin and initiates the blood clotting cascades in a discrete dose of blood fluid so that it can be transported to a wound in a patient such that the treated blood fluid dose can come into contact with the patient proximate the wound such that the clotting cascades can be completed proximate the wound, thereby forming a clot in the wound which prevents fluid from passing through the wound. The invention provides the opportunity to manipulate the blood fluid in respects needed to achieve the desired clot formation in the wound. This typically includes the elements of neutralizing or substantially eliminating the effects of anti-coagulating drugs such as heparin when found in the blood fluid which is treated and also those natural elements of the clotting cascade and of basic clot formation.

The steps of treating a blood fluid with an agent which substantially reduces the anticoagulation effect present in the blood fluid includes binding any heparin present in a discrete dose of blood fluid and thus removing the negatively charged anti-coagulating either by simple ion exchange, by substantially irreversible ion binding or by administering an agent that chemically inactivates, incapacitates, degrades, neutralizes or destroys the heparin molecule. Also included in preferred treatment are the elements in the intrinsic and extrinsic clotting cascade mechanism for human blood fluid including activation of blood factors VII, VIII and XII which in turn lead, to eventually to thrombin formation which lead to the conversion of the naturally occurring blood product fibrinogen into a solid phase fibrin clot. By containing blood fluid to be used in wound sealing and eliminating the effects of anti-coagulating agents and initiating and continuing the natural clotting cascades under controlled sterile conditions, the present invention method and apparatus provides the opportunity to manipulate blood fluid used to form a wound sealing clot in many ways not possible before.

The mechanism and method to contain the blood fluid, under sterile conditions, can be achieved in any relationship with respect to the patient's body. The mechanism to receive and contain the blood fluid can be in fluid communication with a patient's body and blood supply by means of any device commonly used for patient vascular access, such as catheters, introducer sheaths, needles, angiocaths or other commonly used devices. The mechanism, in this situation, can be completely outside of the body, adjacent to the body, partially in the body as with an introducer sheath or it can be contained completely within the body such as with an expandable balloon. The mechanism to receive and contain the blood fluid can also be separable from any direct fluid communication with the body. The mechanism can be a stand alone device or system to which blood fluid, previously drawn or gathered, can be brought and within which the steps of heparin neutralization and clotting cascade initiation can be achieved. The thus treated blood fluid can then be delivered to the wound site by any of various means including a needle, introducer sheath, catheter, etc. An apparatus to be used for sterile enclosed containment of the blood fluid may exist in many forms. A representative example of such enclosures would include syringes, cartridges, vials, test tubes, jars, bags, balloons, pouches, trays, dishes, bowls, tubing, catheters, cannulae in general, and the like. A common feature to such containers would include the ability to keep the container substantially enclosed thereby preventing a level of contamination or loss of sterility unacceptable to the user. In practice, one or more containers may used separately or in combination. For example, a syringe connected to a catheter may be regarded as two containers or a single container with a transfer means, depending on the context of the discussion it is used in. Both context are acceptable and not intended to be limiting. Likewise, a single container may have one or more chambers internal to it. As a result, a single container with multiple chambers may be referred to as a single container or multiple containers. Again, both referrals are acceptable and should be interpreted in the context of the discussion and not be interpreted as to be limiting. Generally, the containers have at least one fluid communication element associated with it which connects the inside to the outside of the container. A fluid communication element may have a normally open hole such as a luer fitting, a normally closed hole such as a septum, or a selective opening such as a molecular sieve or semi-permeable membrane, and the like.

In providing the user with a functional construct of the present invention, it may be desirable to provide the user with a kit of components bundled together for ease of use. As with other aspects of the invention illustrated earlier, this invention can take many forms and is typically dependent on clinical application, user preferences, and the like. As such, the following is merely an illustrative example of what a kit may consist of and should not be interpreted as a limitation of the present invention. For the sake of continuity with previous illustrations, this illustration will be in the context of a typical kit for use with minimally invasive angiographic procedures and the like. Thus, the kit may contain a wound closure apparatus or clotting cascade initiation apparatus of the present invention singularly or in combination with one or more of the following: an introducer, guidewire, dilator, obturator, collapsible catheter sheath, Seldinger needle, balloon catheter, infusion catheter, stent, scalpel, suture line, needle, pouch, tray, tray lid, instructions for use, adhesive identification label, sterility indicator, and the like.

Heparin neutralization can most effectively be achieved by either binding and thereby removing substantially all of the heparin from an aliquot of blood by exposing the blood to a pharmacological agent that serves to bind so as to remove, chemically degrade or otherwise inactivate the heparin. Hirudin, which is also an anti-coagulating agent, is similar to heparin in that they are both negatively charged molecules when contained within a aqueous system such as blood or a blood fluid. As such, both will generally bind to positively charged polymers such as DEAE Cellulose and the like. Polyethyleneimine (PEI) is an example of a preferred agent useful in binding and thus removing negatively charged anti-coagulating agents such as heparin from a discrete aliquot of blood. Polyethyleneimine is a branched chain polymer having a ratio of 1:2:1 of primary:secondary:tertiary amines with a branching site every 3 to 3.5 nitrogen atoms and a general backbone of $(CH_2CH_2NH)_x$. The nitrogen atoms are protonated so as to achieve a positive cationic charge. Heparin is highly sulfated resulting in a negative charge and is therefore readily attracted to, substantially irreversibly bound by and effectively removed from blood fluids when exposed to a biomaterial substrate or other surface coated with immobilized polyethyleneimine. Use of diethylaminoethyl cellulose (DEAE), a positively charged ion exchange polymer or resin is another material that can be utilized to attract, bind and remove heparin from a sample of blood, although its use has provided less effective results in the hands of the present inventors. Another reliable method to attract, bind and remove heparin is by use of a surface treatment, as opposed to a coating, one such surface treatment being aminoacetylization. Aminoacetylization, as described by Shiomi, provides a dense concentration of positively charged functional groups on the surface of a chosen substrate. These cationic surface charges work in the same manner as the positively charged nitrogen atoms present with polyethyleneimine.

Heparinase is an example of a material that will chemically break heparin down, thus rendering it ineffective. Heparinase is a naturally occurring blood component. Protamine sulfate is another material that will chemically inactivate heparin. In addition, platelet factor IV (PF4) is another substance that is capable of reversing heparin in a protamine like fashion. In addition, heparin reversal can be achieved by immobilization of protamine onto a suitable substrate, thus providing the same reversal capability as achieved using positively charged substances. Yet another approach is to override the heparin by exposing the blood fluid by exposing it to surface immobilized thrombin within the sterile containment chamber.

A cross-linked fibrin clot is a gelatinous-like substance with a very high water content. An additional element of this invention is a means to partially reduce the free fluid component of the clot so as to produce a firmer and possibly stronger clot substance. Any of various materials are capable of absorbing and binding water when blood is passed over them.

As used herein, procoagulant refers to any process, activity, material or substance that serves to initiate, continue or accelerate a clotting cascade. Human blood naturally has a redundant system for achieving clot formation as a natural, efficient way of protecting against hemorrhaging. The two arms of this redundant system are the extrinsic and the intrinsic clotting cascade. Each cascade includes a complex, sequential series of steps or stages during which a blood factor necessary for clot formation is activated, the activated blood factor, furthering the cascade, will initiate steps causing the formation of controlled amounts of the powerful, natural clot inducing substance thrombin. The thrombin will, in turn, work to convert the naturally circulating, fluid phase plasma protein fibrinogen into a cross-linked, solid phase mass known as a fibrin clot. It will be appreciated that a fibrin clot is an effective, natural agent to achieve hemostasis, or the cessation of bleeding, from a wound.

The intrinsic clotting cascade can be initiated and then progress through a number of different sub-pathways. Blood factor XII can be initiated and converted into activated blood factor XII, known as XIIa, by means of contact with the surface of biocompatible materials as are used widely in the practice of medicine. All materials, to varying degree, will activate blood factor XII into XIIa, depending upon a complex series of variables including material type, surface area, and exposure time. An example of a material beneficially used to activate blood factor XII is cotton, such as is used in bandages and in the packing used by a dentist. Cotton is also effective in binding water which will aid in eventually producing a firmer and stronger clot. Any of various polymers conventionally used for medical devices; polyethylene, polycarbonate, polypropylene, ethylenevinylaichohol (EVAL), cellulose acetate, urethane and silicone being examples, materials such as glass, metal or ceramics also used in medical devices or, as is the case in a preferred embodiment of this invention, any of the above materials used as a substrate for a second biomaterial which is coated upon the substrate and that also has the ability to neutralize the anti-coagulating drug heparin, can be beneficially used to activate blood factor XII. By means of manipulation of the type and amount of material, its configuration, density, porosity and overall surface area, the degree to which a discrete dose of blood fluid, drawn through a substantially sterile containment chamber containing the material, can be exposed and have blood factor XII converted to XIIa, can be controlled. Blood factor VIII, a constituent within another of the intrinsic sub-pathways, is known to be converted to activated blood factor VIII (or VIIIa) by means of mechanical agitation or shear. Blood factor VIIIa, as with XIIa, initiates a series of enzymatic reactions that leads to the production of controlled amounts of thrombin. Blood exposed to mechanical agitation, such as shear, will generate varying degrees of Blood factor VIIIa in proportion to the amount or degree of agitation induced. For this reason, manufacturers and designers of medical devices that require the transport and manipulation of large amounts of blood fluid, such as oxygenators, dialysis machines, etc. will go to great lengths to minimize the amount of agitation and shear generated during the handling of the blood so as to minimize the amount of blood factor VIIIa generated. Conversely, when the controlled activation of blood factor VIII is desired, such as when a discrete dose of blood thus treated will be used to create hemostasis in a wound, the amount of agitation or shear induced when transporting a discrete dose of blood fluid can be manipulated by control of various design features in the transport mechanism. Mechanical agitation or shear, measured in units of l/seconds (reciprocal seconds), with ideally at least 500 l/seconds and, preferably, and increasingly more up to about 1200 l/seconds, but with continued benefit beyond 1200 l/seconds up to the point of destruction or lysis of blood cells from excessive manipulation, can be beneficially used to produce blood factor VIIIa and then used to treat a wound to control bleeding.

The extrinsic clotting cascade is the second arm of the human blood fluid clot forming system. The extrinsic system works when blood fluid which has not been inhibited from clotting by use of drugs, is exposed to wound tissue or tissue beyond the interior lining of arteries, veins or capillaries. This exposure serves to activate blood factor VII to activated blood factor VII or VIIa. Blood factor VIIa, as with XIIa and VIIIa will lead to the formation of controlled amounts of thrombin and eventually to a fibrin clot useful for achieving and maintaining hemostasis. Blood fluid which has had the effects of heparin neutralized in a sterile containment chamber and which may or may not have had blood factors XII and VIII activated, and that is transported to the site of a wound will work to convert blood factor VII to VIIIa and this will lead to the formation of a fibrin clot that will serve to control bleeding in the wound. As a preferred embodiment, the combining of heparin inactivation, blood factor XII activation from biomaterial contact, blood factor VIII activation from induction of mechanical shear and blood factor VII activation from transport of the blood fluid into a position of contact with wound tissue, preferably utilizing all pathways either sequentially or simultaneously. Heparin inactivation is recognized as a necessary step and the most significant factor among these various elements as without this activity the blood fluid will not readily be converted to a solid phase fibrin clot even if various blood factors are activated. It is also recognized that, to some extent, activation of blood factors such as VII, VIII and XII can not be avoided when manipulating the blood fluid and using it as a hemostatic agent.

The preferred embodiment teaches a method to utilize all of the above listed factors in an efficient system that also maximizes or optimizes the effect of each step. In one preferred embodiment, an enclosed chamber, such as a syringe, produced from an injection moldable polymer such as polycarbonate and having an opening on one end devised to releaseably attach, such as by means of a luer fitting, standard percutaneous access devices, such as hemostasis sheaths, catheters, needles or angiocaths and having a movable plunger, common to a syringe on the other end of the enclosed chamber, is partially filled with a coated matrix of biomaterial. The preferred coating is immobilized polyethyleneimine and the preferred porous matrix being glass beads or polypropylene fibers. The coated porous matrix being contained by a porous membrane or filter with openings smaller than the size of the glass beads or polypropylene fibers. The coated porous matrix being of sufficient quantity in terms of surface area to assure effective binding and thus removal of at least about 5 units of heparin, preferably at least about 10 units, more preferably at least about 20 and even more preferably at least about 40 units, and with sufficient porosity, density and surface area to assure at least 500 l/seconds of mechanical agitation or shear and preferable more up to 1200 l/seconds and more than 1200 l/seconds up to the point of blood cell destruction. The chamber of the syringe not filled with the porous matrix is preferably of sufficient volume to receive a volume of blood sufficient to treat a wound site, this volume is preferably at least about 1 ml, more preferably about 2 or more ml and most preferably about 5 ml, however, more than about 5 ml does not detract from the usefulness of the invention.

In use, the present device is connected by a luer fitting to a vascular access device already in place for use in a medical procedure. This connection would typically be made to the side-arm of a hemostasis valve 33, interconnected with a sheath 34 and would, therefore, be in direct fluid communication with a blood vessel accessed for the procedure and thus having an access site or arteriotomy in the case of an artery. A discrete dose of blood is preferably drawn out of the artery through the sheath 34 into the side-arm 29 and then into the sterile containment chamber through the coated porous matrix within the chamber and then into a receiving chamber in the syringe as the syringe plunger is partially withdrawn. As the blood sample passes through the porous coated matrix substantially all trace of the heparin is preferably bound and, therefore, removed by the positively charged polyethyleneimine coating on the substrate surface; the porous matrix will preferably have sufficient surface area and tortuosity to activate the blood factor XII contained in the blood dose, the porous matrix also having sufficient porosity and tortuosity to achieve at least 500 l/seconds and preferably 1200 l/seconds of mechanical agitation or shear so as to activate blood factor VIII contained in the blood dose. The sheath then being pulled back by the physician to a point just outside of the accessed artery and therefore the end of the sheath now being positioned just outside of the arteriotomy and within the soft tissue wound. The plunger of the syringe then being advanced thus pushing the blood sample back through the system and into the wound area thus activating blood factor VII. The treated blood can be either transported back through the porous matrix furthering the intrinsic clotting cascade activation mechanisms or delivered through a more direct path avoiding the porous matrix. The heparin inactivated blood with the intrinsic and extrinsic clotting cascade mechanisms activated by means of blood factor VII, VIII and XII activation then advancing to a solid phase fibrin clot useful for creating hemostasis at the arteriotomy and the wound site. The preferred embodiments of the apparatus of the present invention may be highly varied and is typically dependent on the individual application considering clinical situation, physician preference, and the like. As such, a clinical situation is selected and physician preference stated here for purposes of providing an illustrative example of one form of the invention apparatus. Presentation of this scenario is intended to be an instructive example of how the invention may be adapted to individual needs and should not be interpreted in a limited context as to how the invention applies. When used as a reference, those skilled in the art will be able to alter configurations and attributes of the apparatus to the same and other needs without departing from the scope and spirit of the present invention. The present example selected is that of post-introducer arterial wound closure following an angiographic procedure and the like. Post-introducer arterial wound closure typically involves the closure of a wound within an arterial wall such as the femoral artery, radial artery, and the like. Such wounds are typically subcutaneous in the sense that the artery is covered by tissue rather than being exposed by cut down through the tissue until the artery is visible to the practitioner.

In the present illustrations, the preferred apparatus is configured for use typically with autologous whole blood. FIG. 1 represents a completed apparatus assembly in-place attached to the introducer and in the patient as it would typically be used. Introducer/hemostasis sheath 32 is placed through the patients skin 41, i.e., percutaneously with the distal end of the sheath within an artery 36. Autologous blood is drawn back from the distal end of the sheath 34 by means of pulling back on the syringe plunger. During this process the blood is passed through the heparin removing and clotting cascade initiating chamber 20 and into the barrel of the syringe 3. The sheath 34 is then withdrawn to a position just outside of the artery 36 as is alternately determined use a pulsitile indicator (not shown). The syringe plunger 2 is then advanced by expelling the blood in the barrel of the syringe 3 back through the heparin binding and clotting cascade initiating chamber 20, then back through the sheath 32 and expelling it into the tissue 41 adjacent to the artery 36 where the clotting cascade comes to completion.

FIG. 2 shows a combination syringe-heparin binding and clotting cascade initiating apparatus. Within the syringe barrel 3 a heparin binding and intrinsic clotting cascade initiating material 14' preferably including polyethyleneimine (PEI) coated glass beads or ethylenevinylalcohol (EVAL) surface treated by aminoacetylization. A membrane filter or screen 43a and 43b, respectively is located on either side of the procoagulant materials 14'.

FIG. 3 shows a 12 cc polymer syringe 3" consisting of a plunger rod 2" connected to a fluid sealing piston 4" is slidingly placed within the syringe 3", thereby allowing the syringe to receive and expel fluids through the distal port 5" of the syringe 3". A three-way connector 7" permits fluid communication between its three ports. Luer lock cylinder cap fittings 8" and 10", preferably made of polycarbonate, are used to form a container when assembled to the ends of cylinder 9, also preferably made of polycarbonate.

The following examples achieve a suitable surface capable of removing heparin from solution.

COATING PROCESS USING POLYETHYLENEIMINE (PEI)

The following example coats out a surface with PEI by solution phase coating as follows:
1. PEI is made in solution in the range of 0.01% to 1.0% PEI in a 0.3% borate buffer solution
2. The material is coated with the PEI for 60 minutes
3. The material is rinsed with 20×volume of sterile water
4. The material is heated at 50 C for 24 hours

COATING PROCESS USING DERIVATIZED POLYETHYLENEIMINE (dPEI)

The following example coats out a surface with derivatized PEI (dPEI); e.g butylated PEI from BioInteraction, Ltd., Redding, United Kingdom; by solution phase coating as follows:
1. dPEI is made in solution in the range of 0.01% to 1.0% dPEI in a 0.3% borate buffer solution
2. The material is coated with the dPEI for 60 minutes
3. The material is rinsed with 20×volume of sterile water
4. The material is heated at 50 C. for 24 hours

COATING PROCESS USING POLYETHYLENEIMINE (PEI)+CROSS-LINKER

This process involves first priming the surface by immersing the material in a dilute solution of PEI with a cross-linker. The cross-linkers that have demonstrated successful coating include: glutaraldehyde, crotenaldehyde, carbonyl diimidazole, ethylene glycol diacrylate, butane diol diglycidyl ether, pentaerythritol-tris-(N-aridinyl) proprionate (XAMA-7 from Sigma Chemical Co., St. Louis, Mo.), Polyethyleneoxide diglycidyl ether.

The above cross-linkers have in common: they are multifunctional, water soluble, and they react with amine groups (they cross-link PEI).

Reagents
1. 0.03% borate buffer pH9.0
2. 1% Citrate buffer pH 3.0
3. 1% Citrate buffer pH 3.9

4. 0.1% PEI+0.1% CROSS-LINKER (any of the above mentioned cross-linkers)

5. 0.03% Dextran Sulfate 6. 0.04% Polyethyleneimine

Procedure

1. Immerse objects in reagent 4 above for 30 minutes at room temperature
2. Immerse objects in reagent 5 above for 10 minutes at 50 C.
3. Immerse objects in reagent 4 above for 30 minutes at room temperature
4. Immerse in reagent 5 above for 10 minutes at room temperature During the process the surface is exposed to a solution of dextran sulfate, followed by a repeat of the initial PEI+CROSS-LINKER, dextran sulfate, and then a solution of PEI that does not contain the cross-linker.

COATING PROCESS USING POLYETHYLENEIMINE (PEI)+POLYACRYLIC ACID (PAA)

The deposition of PEI on the material surface can be greatly enhanced by the addition of solution phase coating step that adds PAA to the surface. The PAA must be at a mW greater than 3,000,000. The addition of a PAA step can enhance PEI deposition for both material coating with and without a crossliner. The PAA is made as a 0.06% w/v Polyacrylic Acid (PAA). The addition of the PAA would be applied after an initial deposition of PEI, as described above, and following by an additional PEI step.

COATING PROCESS USING POLYLYSINE

The above described process can also be achieved by incorporating polylysine in place of PEI as the material to surface deposit at the surface to achieve removal of heparin.

SURFACE MODIFICATION PROCESS USING AMINOACETYLIZATION

An alternative to coating to provide a surface that can remove heparin, is to modify a surface so that it can remove heparin. One such approach was described by Shiomi in which heparin was ionically bound onto the surface of an ethylene vinyl copolymer membrane which was derivatized by aminoacetylization to produce cationic surface charges. The amount of bound heparin was proportional to the ion exchange capacity of the aminoacetalized membrane and the maximal amount obtained was 96 Unit/cm2 (0.59 mg/cm2).

1. Ethylene Vinyl Alcohol (EVAL) or Cellulose Acetate membranes are prepared for surface modification.
2. 2,3-[3-(dimethylamino)propylamino]propionaldehyde acetal (APA) is obtained for aminoacetylization product.
3. The EVAL or Cellulose Acetate membranes are placed in a mixture of 2.5 g APA, 8.0 g 35% HCL aqueous solution, 16.0 g NaCl, and 73 g water. The mixture is slowly stirred for 4 hours at 50 C. to achieve aminoacetylization of the membrane
4. The aminoacetylized membrane is rensis with water and is ready for use for removal of heparin from whole blood These alternatives merely illustrate examples of the present invention. It is to be understood, however, that even though numerous characteristics and advantages of the present invention have been set forth in the foregoing description, together with detail so the structure and function of present invention, the sequence or order of the specific steps, or the actual compositions or materials used may vary somewhat. Furthermore, it will be appreciated that this disclosure is illustrative only and that changes may be made in detail, especially in matters of shape, size, arrangement of parts or sequence or elements of aspects of the invention within the principles of the invention to the full extent indicated by the broad general meaning of the terms in which the appended claims, which form a further part hereof, are expressed.

What is claimed is:

1. A method of closing a wound in a patient, the method comprising the steps of:
    a) treating a blood fluid with an agent which substantially reduces the anti-coagulating effect of a negatively charged anti-coagulating agent present in the blood fluid prior to treatment, the agent interacting with a negatively charged anti-coagulating agent in the blood fluid in a manner selected from the group consisting of binding the negatively charged anti-coagulating agent so as to substantially remove the negatively charged anti-coagulating agent from the blood fluid, degrading a negatively charged anti-coagulating agent so as to make the negatively charged anti-coagulating agent ineffective as an anti-coagulating agent and binding to the negatively charged anti-coagulating agent so as to make the negatively charged anti-coagulating agent substantially ineffective as an anti-coagulating agent which inhibits or impedes either the initiation or the continuance of a clotting cascade within the blood fluid; and
    b) transporting the treated blood fluid to the wound in the patient such that the blood fluid comes into contact with the patient proximate the wound and the clotting cascade comes generally to a conclusion and a clot forms proximate the wound such that the clot prevents fluid from passing through the wound.

2. The method of claim 1, wherein the step of treating the blood fluid includes treating the blood fluid with a procoagulating agent to initiate a clotting cascade during a first time period such that at least a portion of the blood fluid will form a clot of blood during a second time period subsequent to the first time period, the blood fluid containing sufficient blood components to enable a portion of the blood fluid to clot during the second time period subsequent to the initiation of the clotting cascade during the first time period; the blood fluid being selected from the group consisting of whole blood, natural components of whole blood, whether derived from whole blood, blood extracts, or products of ex-vivo cell cultures, and procoagulating agents which assist in or enhance the clotting or coagulation of the blood fluid.

3. The method of claim 2, wherein the procoagulating agent within the sterile containment chamber is sufficient to initiate a clotting cascade within the blood fluid and the step of treating the blood fluid will result in a blood fluid which contains up to about 25 micrograms of thrombin per milliliter of blood fluid.

4. The method of claim 1, wherein the negatively charged anti-coagulating agent is selected from the group consisting of heparin and hirudin.

5. The method of claim 1, wherein the negatively charged anti-coagulating agent is heparin.

6. The method of claim 1, wherein the agent which substantially reduces the anticoagulating effect of the negatively charged anti-coagulating agent is a positively charged functional group bound to a surface within the sterile containment chamber.

7. The method of claim 1, wherein the agent which substantially reduces the anti-coagulating effect of the negatively charged anti-coagulating agent is positively charged polymer which is surface coated upon an exposed surface within the sterile containment chamber.

8. The method of claim 1, wherein the agent which substantially reduces the anti-coagulating effect of the negatively charged anti-coagulating agent is a surface coated polymer selected from the group consisting of PEI and dPEI.

9. The method of claim 1, wherein the agent which substantially reduces the anti-coagulating effect of the negatively charged anti-coagulating agent is surface coated PEI.

10. An apparatus within which a blood fluid can be received, the blood fluid being useful for treatment of a wound within a patient, said apparatus comprising:

a substantially enclosed sterile containment chamber within which the blood fluid can be received, the substantially enclosed sterile containment chamber containing an agent which substantially reduces the anti-coagulating effect of a negatively charged anti-coagulating agent present in the blood fluid prior to treatment, the agent interacting with a negatively charged anti-coagulating agent in the blood fluid in a manner selected from the group consisting of binding the negatively charged anti-coagulating agent so as to substantially remove the negatively charged anti-coagulating agent from the blood fluid, degrading a negatively charged anti-coagulating agent so as to make the negatively charged anti-coagulating agent ineffective as an anti-coagulating agent and binding to the negatively charged anti-coagulating agent so as to make the negatively charged anti-coagulating agent substantially ineffective as an anti-coagulating agent which inhibits or impedes either the initiation or the continuance of a clotting cascade within the blood fluid;

a procoagulating agent within the sterile containment chamber; wherein a clotting cascade is initiated when the blood fluid is received in the sterile containment chamber and exposed to the procoagulating agent within the chamber, and the blood fluid can be delivered to a wound subsequent to the initiation of the clotting cascade, such that the clotting cascade, initiated within the sterile containment chamber prior to the delivery of the blood fluid to the wound, can be completed within the wound and a clot can form within the wound when the clotting cascade is completed.

11. The apparatus of claim 10, wherein the negatively charged anti-coagulating agent is selected from the group consisting of heparin and hirudin.

12. The apparatus of claim 10, wherein the negatively charged anti-coagulating agent is heparin.

13. The apparatus of claim 10, wherein the procoagulating agent within the sterile containment chamber is sufficient to initiate a clotting cascade within the blood fluid and the step of treating the blood fluid will result in a blood fluid which contains up to about 25 micrograms of thrombin per milliliter of blood fluid.

14. The apparatus of claim 10, wherein the agent which substantially reduces the anti-coagulating effect of the negatively charged anti-coagulating agent is a positively charged functional group bound to a surface within the sterile containment chamber.

15. The apparatus of claim 10, wherein the agent which substantially reduces the anti-coagulating effect of the negatively charged anti-coagulating agent is positively charged polymer which is surface coated upon an exposed surface within the sterile containment chamber.

16. The apparatus of claim 10, wherein the agent which substantially reduces the anti-coagulating effect of the negatively charged anti-coagulating agent is a surface coated polymer selected from the group consisting of PEI and dPEI.

17. The apparatus of claim 10, wherein the agent which substantially reduces the anti-coagulating effect of the negatively charged anti-coagulating agent is surface coated PEI.

18. A method of closing a wound in a patient, said method comprising the steps of:

a) providing a clotting cascade initiation apparatus within which a blood fluid can be received, said apparatus including a substantially enclosed sterile containment chamber within which the blood fluid can be received; the containment chamber containing a procoagulating agent within the substantially enclosed sterile containment chamber; wherein a clotting cascade can be initiated when the blood fluid is placed into the sterile containment chamber and thereby exposed to the procoagulating agent; the containment chamber further containing an agent which substantially reduces the anti-coagulating effect of a negatively charged anti-coagulating agent present in the blood fluid prior to treatment, the agent interacting with a negatively charged anti-coagulating agent in the blood fluid in a manner selected from the group consisting of binding the negatively charged anti-coagulating agent so as to substantially remove the negatively charged anti-coagulating agent from the blood fluid, degrading a negatively charged anti-coagulating agent so as to make the negatively charged anti-coagulating agent ineffective as an anti-coagulating agent and binding to the negatively charged anti-coagulating agent so as to make the negatively charged anti-coagulating agent substantially ineffective as an anti-coagulating agent which inhibits or impedes either the initiation or the continuance of a clotting cascade within the blood fluid;

b) placing a sufficient amount of blood fluid into the containment chamber to provide a sufficient amount of blood fluid to enable the blood fluid to knit together to form a clot proximate the wound once the clotting cascade is initiated; and c) delivering the blood fluid to the wound subsequent to the initiation of the clotting cascade in the containment chamber such that the clotting cascade can be completed and a clot can form within the wound after the blood fluid is delivered to the wound.

19. The method of claim 18, wherein the procoagulating agent within the sterile containment chamber is sufficient to initiate a clotting cascade within the blood fluid and the step of treating the blood fluid will result in a blood fluid which contains up to about 25 micrograms of thrombin per milliliter of blood fluid.

* * * * *

UNITED STATES PATENT AND TRADEMARK OFFICE
CERTIFICATE OF CORRECTION

PATENT NO.   : 6,482,223 B1                                                  Page 1 of 1
DATED        : November 19, 2002
INVENTOR(S)  : Karol L. Nowakowski et al.

It is certified that error appears in the above-identified patent and that said Letters Patent is hereby corrected as shown below:

Column 1,
Line 34, delete "ample" and insert therefor -- sample --;

Column 11,
Line 23, delete "ethlenevinylaichohol" and insert therefor -- ethlenevinylalchohol --;

Column 12
Line 12, delete "VIIIa" and insert therefor -- VIIa --;

Column 13,
Line 1, delete "side-ann" and insert therefor -- side-arm --;

Column 14,
Line 40, delete "BioInteraction" and insert therefor -- BioInteraction --;

Signed and Sealed this

Seventh Day of October, 2003

JAMES E. ROGAN
*Director of the United States Patent and Trademark Office*